United States Patent

Seneker et al.

Patent Number: 5,288,899
Date of Patent: Feb. 22, 1994

[54] LIQUIFICATION OF DIPHENYLMETHANE DIISOCYANATE BY PARTIALLY REACTING THE ISOCYANATE GROUPS WITH BLOCKING AGENTS

[75] Inventors: Stephen D. Seneker, Paden City; Scott A. Kane, New Martinsville; James W. Rosthauser, Glendale, all of W. Va.

[73] Assignee: Miles Inc., Pittsburgh, Pa.

[21] Appl. No.: 85,235

[22] Filed: Jun. 30, 1993

[51] Int. Cl.⁵ .......................................... C07C 249/00
[52] U.S. Cl. ................................. 560/330; 560/331
[58] Field of Search ............................. 560/330, 331

[56] References Cited

U.S. PATENT DOCUMENTS

| | | | |
|---|---|---|---|
| 3,151,162 | 10/1964 | Fischer et al. | 260/453 |
| 3,384,653 | 5/1968 | Erner et al. | 260/453 |
| 3,394,165 | 7/1968 | McClellan et al. | 260/453 |
| 3,449,256 | 6/1969 | Farrissey, Jr. et al. | 252/182 |
| 3,640,966 | 2/1972 | Hennig et al. | 260/77.5 R |
| 3,641,093 | 2/1972 | Brooks et al. | 260/453 AR |
| 3,644,457 | 2/1972 | König et al. | 260/453 SP |
| 3,674,828 | 7/1972 | Brooks et al. | 260/453 P |
| 3,701,796 | 10/1972 | Saaty et al. | 260/453 SP |
| 3,883,571 | 5/1975 | Allport et al. | 260/453 AM |
| 4,014,935 | 3/1977 | Ibbotson | 260/566 R |
| 4,031,026 | 6/1977 | Ibbotson | 252/182 |
| 4,055,548 | 10/1977 | Carleton et al. | 260/77.5 AT |
| 4,088,665 | 5/1978 | Findeisen et al. | 260/453 AM |
| 4,102,833 | 7/1978 | Salisbury | 521/159 |
| 4,115,429 | 9/1978 | Reiff et al. | 260/453 SP |
| 4,118,411 | 10/1978 | Reiff et al. | 260/453 SP |
| 4,154,752 | 5/1979 | Sundermann et al. | 260/453 SP |
| 4,177,205 | 12/1979 | Schaaf et al. | 260/453 AM |
| 4,229,347 | 10/1980 | Holt et al. | 260/239 A |
| 4,261,852 | 4/1981 | Carroll et al. | 528/59 |
| 4,321,333 | 3/1982 | Alberino et al. | 521/159 |
| 4,332,742 | 6/1982 | Allen | 260/453 SP |
| 4,490,300 | 12/1984 | Allen et al. | 260/453 SP |
| 4,490,301 | 12/1984 | Pantone et al. | 260/453 SP |
| 4,490,302 | 12/1984 | Ma et al. | 260/453 AM |
| 4,539,156 | 9/1985 | Dewhurst et al. | 260/453 SP |
| 4,539,157 | 9/1985 | Dewhurst et al. | 260/453 SP |
| 4,539,158 | 9/1985 | Dewhurst et al. | 260/453 SP |
| 4,611,083 | 9/1986 | Buethe et al. | 560/351 |
| 4,686,242 | 8/1987 | Turner et al. | 521/137 |
| 4,689,356 | 8/1987 | Peffley et al. | 521/159 |
| 4,868,298 | 9/1989 | Brinkman | 540/525 |
| 4,883,909 | 11/1989 | Slack | 560/351 |
| 5,142,019 | 8/1992 | Sundararaman et al. | 528/271 |

Primary Examiner—Arthur C. Prescott
Attorney, Agent, or Firm—Joseph C. Gil; N. Denise Brown

[57] ABSTRACT

The present invention relates to a liquid, storage-stable isocyanate having a viscosity of less than 100,000 mPa.s at 25° C. and an isocyanate content of from about 10 to 29% by weight, and is prepared by reacting a solid or semi-solid diphenylmethane diisocyanate with a blocking agent. More generally, the liquid isocyanate is prepared by reacting the solid or semi-solid diphenylmethane diisocyanate with the blocking agent in quantities such that from 7 to 55% of the isocyanate groups are blocked. Preferred blocking agents are the ketoximes, and mixtures thereof.

6 Claims, No Drawings

LIQUIFICATION OF DIPHENYLMETHANE DIISOCYANATE BY PARTIALLY REACTING THE ISOCYANATE GROUPS WITH BLOCKING AGENTS

BACKGROUND OF THE INVENTION

The present invention relates to liquid, storage-stable isocyanates prepared by reacting solid or semi-solid diphenylmethane diisocyanates. The most commercially important diphenylmethane diisocyanates which are solid at room temperature are 4,4'-diphenylmethane diisocyanate and the 2,4'-isomer thereof, which melt at 39° C. and 34.5° C., respectively.

Diisocyanates which are liquid at room temperature have obvious advantages compared to those diisocyanates which are fused solids or slurries at ambient temperature. A liquid is easier to pump and less expensive to transport. A liquid has a homogeneous composition as supplied without the need to homogenize it at elevated temperatures as is the case with slurries or fused solids. In the production of polyurethanes, a liquid can be added easily by weight or volume, and combined with suitable coreactants at ambient temperatures. This is safer than using the materials at elevated temperatures due to the lower vapor pressure of the materials at room temperature.

Numerous patents have issued relating to the liquefication of diphenylmethane diisocyanate. See, for example, U.S. Pat. Nos. 3,152,162; 3,384,653; 3,394,165; 3,449,256; 3,640,966; 3,641,093; 3,674,828; 3,701,796; 3,883,571; 4,014,935; 4,055,548; 4,088,665; 4,031,026; 4,102,833; 4,115,429; 4,118,411; 4,154,752; 4,177,205; 4,229,347; 4,261,852; 4,321,333; 4,332,742; 4,490,300; 4,490,301; 4,490,302; 4,539,156; 4,539,157; 4,539,158; and 4,883,909. Generally, these related to processes which chemically modify the diisocyanate, and yield an adduct. A disadvantage common to all of these processes is that they are not reversible to the original diisocyanate.

It is known from U.S. Pat. No. 3,644,457 to react 4,4'- and/or 2,4'-diphenylmethane diisocyanate with a branched aliphatic dihydroxyl compound or polyethers based on 1,2-propylene glycol to produce a product which is liquid at room temperature. In a similar manner, U.S. Pat. No. 4,055,548 teaches that diphenylmethane diisocyanate can be liquefied by reaction with ethylene glycol-based polyethers.

Liquid diphenylmethane diisocyanates have also been produced by reacting diisocyanates having specified 2,4'-isomer contents with propylene and polypropylene glycols and with polyoxyethylene glycols (see e.g. U.S. Pat. Nos. 4,118,411 and 4,115,429).

It has also been proposed to prepare liquid diphenylmethane diisocyanate compositions by reacting the diisocyanates with three separate alkylene glycols, each having at least three carbon atoms (see e.g. U.S. Pat. No. 3,883,571), or by the same reaction wherein at least one of the glycols is dipropylene, tripropylene, or polypropylene glycol (see e.g. U.S. Pat. No. 4,229,347).

U.S. Pat. No. 4,332,742 discloses the preparation of storage-stable, liquid diphenylmethane diisocyanates by reacting the diisocyanate with an N-substituted ethanolamine.

Urea group-containing polyisocyanate mixtures which are liquid at room temperature are also known. See U.S. Pat. No. 4,611,083.

It is also known that diphenylamine diisocyanates and the higher derivatives can form stable prepolymers with primary amine terminated materials having a degree of amination of from 25 to 100%. See U.S. Pat. No. 4,686,242.

Prepolymers are also known which are prepared by reacting amine reacting amine-terminated polyethers with a variety of different isocyanates including diphenylmethane diisocyanates. See U.S. Pat. 4,689,356.

It is an object of this invention to provide diphenylmethane diisocyanates which are storage-stable and liquid at 25° C.

DESCRIPTION OF THE INVENTION

In particular, the present invention is directed to a liquid, storage-stable isocyanate prepared by reacting a solid or semi-solid diphenylmethane diisocyanate with a blocking agent. The prepared liquid isocyanates have an isocyanate group content of from 10 to 29% by weight, and preferably from 11 to 25% by weight; and viscosities of less than 100,000 mPa.s at 25° C. Generally, these isocyanates can be prepared by reacting diphenylmethane diisocyanate with the blocking agent in quantities such that from 7 to 55%, and preferably from 15 to 52%, of the isocyanate groups react with the blocking agent.

As used herein, the term "liquid" is defined as "a solution having a viscosity below 100,000 mPa.s at 25° C. with no crystals visible to the unaided eye". The term "storagestable" means "a clear liquid after 3 weeks at room temperature with no crystals visible to the unaided eye".

A blocking agent is a compound which combines reversibly with diphenylmethane diisocyanate to form a thermally labile adduct that dissociates at temperatures below 180° C. The amount of blocking agent to be used is such that from 7 to 55%, and preferably from 15 to 52%, of the isocyanate groups react with the blocking agent. If less than 7% of the NCO groups are blocked, the solutions do not remain as clear liquids. Also, viscosity increases significantly as the percent of blocked isocyanate groups increases. The range of from 7 to 55% of blocked isocyanate groups results in a balance between liquidity and viscosity of the prepared isocyanates.

As used herein, the term diphenylmethane diisocyanate refers to 4,4'-diphenylmethane diisocyanate, 2,4'-diphenylmethane diisocyanate, 2,2'-diphenylmethane diisocyanate, and mixtures thereof which are solids or semi-solids at room temperature. Certain mixtures of 2,2-, 2,4'-, and 4,4'-diphenylmethane diisocyanate are liquids at room temperature. These mixtures which are naturally liquids at room temperature are not within the scope of the present invention.

Generally, polyisocyanates of the diphenylmethane series are prepared by the condensation of aniline with formaldehyde to form amines. These amines are subsequently phosgenated to produce the corresponding isocyanates. The various isomers of the monomeric diisocyanate are, subsequently, separated from the higher oligomers by fractional distillation. The solid 4,4'-isomer can thus be isolated in high purity.

Suitable blocking agents which can be used to liquify the diphenylmethane diisocyanate in accordance with the present invention are known blocking agents for polyisocyanates. Examples of these blocking agents include monophenols such as phenol, nonylphenol, the cresols, the trimethyl phenols and the tert butyl phenols; compounds which easily form enols such as acetoacetic ester, acetyl acetone and malonic acid derivatives, e.g., malonic acid diethylester; lactams such as ε-caprolactam and ε-valerolactam; oximes such as acetone oxime, butanone oxime and cyclohexanone oxime; and triazoles such as 1H-1,2,4-triazole. Mixtures of the blocking agents may also be used.

Preferred blocking agents are ketoximes such as methyl-ethyl ketoxime, and methylamyl ketoxime. It is particularly preferred to use mixtures of ketoximes as blocking agents. Such as, for example, equimolar amounts of methylethyl ketoxime and methylamyl ketoxime.

The diphenylmethane diisocyanate is typically charged to the reaction vessel as a melted homogeneous mixture. The temperature of the melt can vary from 40° to 90° C. The reaction vessel is maintained at a temperature which keeps the isocyanate as a homogeneous liquid.

The blocking agent can be added as a liquid or a solid. The reaction temperature is normally maintained below 150° C., preferably between about 50° and 130° C. The reaction is continued until the isocyanate content of the reaction mixture decreases to the theoretical amount or slightly below. The reaction product can have an isocyanate content of about 10 to 29% by weight, and preferably about 11 to 25% by weight. The reaction product is a liquid, storage-stable isocyanate having a viscosity of less than 100,000 mPa.s at 25° C., and does not form crystals after 3 weeks at room temperature.

The liquid, storage-stable isocyanates can be used for the preparation of polyurethanes or polyureas and, in particular, polyurethane or polyurea coatings, adhesives, sealants, patching compounds, and elastomers. These polyurethanes are prepared by the reaction of the isocyanates with glycols and/or polyols, and chain extenders and/or crosslinkers. Polyureas are prepared by the reaction of the isocyanates with diamines and/or polyamines, and chain extenders and/or crosslinkers.

The invention is further illustrated but is not intended to be limited by the following examples in which all parts and percentages are by weight unless otherwise specified.

EXAMPLES

Examples given below: Examples 1 and 7 are comparative examples and were conducted to determine the limits of the invention.

Example 1 (Comparative)

A 500 ml flask was charged with 4,4'-diphenylmethane diisocyanate (200.0 g: 1.600 eq.). The diisocyanate was heated to 60° C. A mixture of methylethyl ketoxime (3.48 g: 0.040 eq.) and methylamyl ketoxime (5.16 g: 0.040 eq.) was added over a 10 minute period. The temperature of the reaction mixture was heated to 90° C., and held at that temperature for about 45 minutes. A 100 g sample of the product (theoretical NCO=30.6%) was poured into a 4 oz. jar and stored at room temperature. After 1 day, the sample began to crystallize.

Example 2

A 500 ml flask was charged with 4,4'-diphenylmethane diisocyanate (200.0 g: 1.600 eq.). The diisocyanate was heated to 60° C., and a mixture of methylethyl ketoxime (6.96 g: 0.080 eq.) and methylamyl ketoxime (10.32 g: 0.080 eq.) was added over a 10 minute period. The mixture was held at 90° C. for about 45 minutes. A 100 g sample of the product (theoretical NCO=27.8%) was poured into a 4 oz. jar and stored at room temperature. After 3 weeks, the viscosity at 25° C. was 37 mPa.s and the solution had remained clear with no evidence of crystal formation.

Example 3

A 500 ml flask was charged with 4,4'-diphenylmethane diisocyanate (200.0 g: 1.600 eq.). The diisocyanate was heated to 60° C., and a mixture of methylethyl ketoxime (13.92 g: 0.160 eq.) and methylamyl ketoxime (20.64 g: 0.160 eq.) was added over a 10 minute period. The temperature of the reaction was held at 90° C. for about 45 minutes. A 100 g sample of the product (theoretical NCO=22.9%) was poured into a 4 oz. jar and stored at room temperature. After storage for 3 weeks at room temperature, the viscosity at 25° C. was 153 mPa.s and the solution has remained clear with no evidence of crystal formation.

Example 4

A 500 ml flask was charged with 4,4'-diphenylmethane diisocyanate (200.0 g: 1.600 eq.) and heated to 60° C. A mixture of methyl ethyl ketoxime (MEKO) (20.88 g: 0.240 eq.) and methyl amyl ketoxime (MAKO) (30.96 g: 0.240 eq.) was added over a 10 minute period. The temperature of the reaction mixture was held at 90° C. for 45 minutes. A 100 g sample of the product (theoretical NCO=18.7%) was poured into a 4 oz. jar and stored at room temperature. After 3 weeks, the viscosity at 25° C. was 337 mPa.s and the solution had remained clear with no evidence of crystal formation.

Example 5

A 500 ml flask was charged with 4,4'-diphenylmethane diisocyanate (200.0 g: 1.600 eq.). The diisocyanate was heated to 60° C., and a mixture of MEKO (27.84 g: 0.320 eq.) and MAKO (41.28 g: 0.320 eq.) was added over a 10 minute period. The temperature of the reaction mixture was held at 90° C. for 45 minutes. A 100 g sample of the product (theoretical NCO=15.0%) was poured into a 4 oz. jar and stored at room temperature. After 3 weeks, the viscosity at 25° C. was 2160 mPa.s and the solution had remained clear with no evidence of crystal formation.

Example 6

A 500 ml flask was charged with 4,4'-diphenylmethane diisocyanate (200.0 g: 1.600 eq.). The diisocyanate was heated to 60° C. and a mixture of MEKO (34.80 g: 0.400 eq.) and MAKO (51.60 g: 0.400) was added over a 10 minute period. The temperature of the reaction mixture was held at 90° C. for about 45 minutes. A 100 g sample of the product (theoretical NCO=11.7%) was poured into a 4 oz. jar and stored at room temperature. After 3 weeks, the viscosity at 25° C. was 14,000 mPa.s and the solution had remained clear with no evidence of crystal formation.

Example 7 (Comparative)

A 500 ml flask was charged with 4,4'-diphenylmethane diisocyanate (200.0 g: 1.600 eq.). The diisocyanate was heated to 60° C. and a mixture of MEKO (41.76.30 g: 0.480 eq.) and MAKO (61.92 g: 0.480 eq.) was added over a 10 minute period. The temperature of the reaction mixture was held at 90° C. for about 45 minutes. A 100 g sample of the product (theoretical NCO=8.9%) was poured into a 4 oz. jar and stored at room temperature. After 3 weeks, the viscosity at 25° C. was greater than 300,000 mPa.s and the solution had remained clear with no evidence of crystal formation.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A liquid, storage-stable isocyanate having a viscosity of less than 100,000 mPa.s at 25° C. and an isocyanate group content of from about 10 to 29% by weight, prepared by reacting
   a) a solid or semi-solid diphenylmethane diisocyanate, and
   b) a blocking agent, or a mixture of two or more blocking agents.

2. The liquid, storage-stable isocyanate of claim 1, wherein said isocyanate group content is from about 11 to 25% by weight.

3. The liquid, storage-stable isocyanate of claim 1, wherein said blocking agent is a ketoxime.

4. The liquid, storage-stable isocyanate of claim 1, wherein said blocking agent is a mixture of two or more ketoximes.

5. The liquid, storage-stable isocyanate of claim 4, wherein said mixture comprises methylethyl ketoxime and methylamyl ketoxime.

6. The liquid, storage-stable isocyanate of claim 5, wherein said methylethyl ketoxime and said methylamyl ketoxime are present in equimolar quantities.

* * * * *